United States Patent [19]

Perozzi et al.

[11] Patent Number: 5,091,112
[45] Date of Patent: Feb. 25, 1992

[54] REDUCING COPPER CORROSIVENESS OF ORGANIC SULFIDES

[75] Inventors: Edmund F. Perozzi, Crestwood, Mo.; John F. Sieberth, Baton Rouge, La.

[73] Assignee: Ethyl Petroleum Additives, Inc., St. Louis, Mo.

[21] Appl. No.: 495,090

[22] Filed: Mar. 19, 1990

[51] Int. Cl.$^5$ .................. C09K 3/00; C23O 11/18
[52] U.S. Cl. .................. 252/387; 252/391; 252/397
[58] Field of Search .................. 568/21, 22, 25; 564/340, 341, 501; 252/387, 391, 397

[56] References Cited

U.S. PATENT DOCUMENTS 3,957,745  5/1976  Cassan .................. 568/22
4,827,040  5/1989  Labat et al. .................. 568/21

OTHER PUBLICATIONS

Morel et al., Synthesis 1980, (11), 918–21, Chemical Abstracts, vol. 94, 1981, Abstract 156247.

*Primary Examiner*—Mukund J. Shah
*Assistant Examiner*—Y. N. Gupta
*Attorney, Agent, or Firm*—John F. Sieberth; Doris M. Thompson

[57] ABSTRACT

Reducing the copper corrosiveness of organic sulfides by treating them with an alkali metal-containing or alkaline earth metal-containing substance capable of dissolving elemental sulfur (e.g., sodium hydroxide, sodium sulfide, etc.). The process is conducted in a substantially homogeneous liquid reaction medium composed of a mixture of water and at least one ketone. Experiments have shown that it is possible by use of this process to reduce the copper corrosiveness to a level below that exhibited by a product formed by treating the same initial organic sulfide in the same way but in a liquid medium composed solely of water.

22 Claims, No Drawings

5,091,112

REDUCING COPPER CORROSIVENESS OF ORGANIC SULFIDES

TECHNICAL FIELD

This invention relates to reducing the copper corrosiveness of sulfur-containing extreme pressure or antiwear agents, such as dihydrocarbyl polysulfides and sulfurized olefins.

BACKGROUND

Japan Kokai 59-10559 describes a process wherein dialkyl polysulfide is treated with an aqueous solution of sodium sulfide at 30°–80° C. for 1–5 hours. The treated product is indicated to have reduced copper corrosiveness, and the applicants in that laid open application express their belief that the reduction in copper corrosiveness is due to a chemical reaction whereby dialkyl tetrasulfide and dialkyl pentasulfide are converted into a less corrosive dialkyl trisulfide.

U.S. Pat. No. 4,827,040 describes a process wherein dialkyl polysulfides are treated with a variety of substances capable of dissolving elemental sulfur, such as alkali metal, alkaline earth and ammoniacal bases, hydrosulfides, alkali metal sulfites, caustic soda, caustic potash, lime, sulfides of sodium, potassium, calcium or ammonium, etc. The treatments when using such inorganic treating agents are conducted in aqueous solutions, and in the process the dialkyl polysulfides are transformed into dialkyl polysulfides having a reduced sulfur content. The most desired product of this process, according to the patentees, is dimethyl disulfide because of its usefulness as a solvent for sulfur in cleaning natural gas conduits.

THE INVENTION

This invention involves, inter alia, the discovery that it is possible to reduce the copper corrosiveness of dialkyl polysulfide to even lower levels than achieved by use of the aqueous solutions of Na$_2$S referred to in Japan Kokai 59-10559. Moreover this invention involves the further discovery that substances capable of dissolving elemental sulfur—i.e., alkali metal containing and alkaline earth metal-containing substances of the type referred to in U.S. Pat. No. 4,827,040—can be used to reduce the copper corrosiveness of dialkyl polysulfides and that by modifying the solvent system, even lower levels of copper corrosiveness can be achieved. And additionally, the copper corrosiveness of dihydrocarbyl polysulfides other than dialkyl polysulfides and of other sulfur-containing materials such as sulfurized olefins can be effectively reduced by the practice of this invention.

In accordance with one of its embodiments, this invention provides a process of reducing the copper corrosiveness of sulfur-containing substances commonly used as extreme pressure or antiwear additives in lubricant compositions, such as dihydrocarbyl polysulfide, sulfurized olefin or like material that is corrosive toward copper which comprises treating the same with an alkali metal-containing or alkaline earth metal-containing substance capable of dissolving elemental sulfur, such treatment being conducted in a substantially homogeneous liquid medium composed of a mixture of water and at least one ketone.

With reference to prior processes such as are described in Japan Kokai 59-10559 and U.S. Pat. No. 4,827,040, this invention provides in a process of treating dialkyl polysulfide with an alkaline inorganic substance capable of dissolving elemental sulfur, the improvement which comprises conducting such treatment in a liquid reaction medium comprising water and at least one ketone such that the resultant dialkyl polysulfide exhibits reduced copper corrosiveness. Indeed, as will be seen in the examples hereinafter, it is possible by use of this process to reduce the copper corrosiveness to a level below that exhibited by a product formed by treating the same initial dialkyl polysulfide in the same way but in a liquid medium composed solely of water.

Still another embodiment of this invention is a dihydrocarbyl polysulfide (most preferably dialkyl polysulfide) formed by a treatment process of this invention, such product being characterized by exhibiting less copper corrosiveness than a product formed from the same initial dihydrocarbyl polysulfide using the same treatment process but in the absence of the ketone or mixture of ketones.

Another particular embodiment of this invention involves reducing the copper corrosiveness of a sulfurized olefinic extreme pressure or antiwear agent which normally exhibits corrosiveness toward copper. This is accomplished by treating such extreme pressure or antiwear agent with an alkali metal-containing or alkaline earth metal-containing substance capable of dissolving elemental sulfur, such treatment being conducted in a liquid medium composed of a mixture of water and one or more ketones.

These and other embodiments, features and advantages of this invention will be still further apparent from the ensuing description and appended claims.

This invention is deemed applicable to any dihydrocarbyl polysulfide and any sulfurized olefin having the adverse property of exhibiting excessive corrosiveness towards copper. A convenient test procedure for use in measuring copper corrosiveness is as follows: A copper coupon approximately 70×15 mm and about 1.25 mm in thickness is cleaned by use of steel wool (0000 grade), washed with heptane, and then with acetone, dried, and weighed to the nearest 0.1 mg. The cleaned coupon is placed in a test tube and covered completely with the composition to be tested, and the system is heated to 121° C., by means of an oil bath maintained at this temperature. After holding the system at 121° C. for three hours, the copper coupon is removed from the test tube, rinsed with heptane and then with acetone. The dried coupon is then rubbed with a paper towel moistened with acetone to remove any surface flakes formed by copper corrosion. The coupon is then air-dried and weighed to the nearest 0.1 mg. The difference in weight as between the initial copper coupon and the coupon after the test represents the extent to which the copper was corroded under the test conditions. Therefore the smaller the weight difference, the less the copper corrosion.

This invention is thus applicable, for example, to individual dihydrocarbyl polysulfides and mixtures of two or more dihydrocarbyl polysulfides wherein in either case at least a portion of polysulfide moiety contains at least four sulfur atoms and wherein the hydrocarbyl groups are alkyl, alkenyl, cycloalkyl, cycloalkylalkyl, aryl, aralkyl, cycloalkenyl, or the like. Such hydrocarbyl groups each can contain any number of carbon atoms, e.g., 100 or more, preferably 50 or less, most preferably up to about 18 carbon atoms, so long as the compound or mixture of compounds exhibits corrosiveness toward copper as seen for example in the above copper corrosion test. Especially preferred dihydrocarbyl polysulfides are dialkyl polysulfides containing 3 to about 18 carbon atoms in each alkyl group, most especially where the polysulfide product being treated pursuant to this invention includes at least dialkyl tetrasulfide and/or dialkyl pentasulfide.

The hydrocarbyl groups of the polysulfides used in the process can be substituted by innocuous substituents, i.e., substituents that do not interfere with or prevent the reduction in copper corrosiveness made possible by the practice of this invention. For example, the hydrocarbyl substituents of the dihydrocarbyl polysulfides may include ether oxygen atoms, thioether sulfur atoms, nitrogen atoms, etc. Thus the polysulfides used in the process of this invention include alkoxyalkyl and (polyalkoxy)alkyl-substituted polysulfides, alkylthioalkyl-substituted polysulfides, aryloxyalkyl polysulfides, dialkylaminoalkyl polysulfides, diarylaminoalkyl polysulfides, and in general, any polysulfide of the formula $R-S_n-R'$ wherein the average value of n is above 3, (preferably 3.5 or above). Thus, the average value for n may vary considerably, but usually is in the range of about 3.5 to about 12 or more. In this formula, each of R and R' is independently, any organic group (cyclic or non-cyclic) containing carbon and hydrogen, and optionally one or more oxygen, sulfur, nitrogen, and/or halogen atoms, all with the proviso that each organic group is bonded to the polysulfide moiety by a carbon-sulfur bond and the compound is corrosive toward copper and is amenable to treatment pursuant to this invention.

This invention is also applicable to other sulfur-containing substances commonly employed as lubricant additives because of their extreme pressure or antiwear properties, with the proviso that such substances exhibit enough corrosiveness toward copper as seen for example in the above copper corrosion test as to warrant a treatment to effect a reduction in such corrosiveness. Substances exhibiting such corrosiveness may be found in such classes of materials as sulfurized olefins, sulfurized oils, and sulfurized fatty acid esters. The sulfurized olefins include products made by sulfurizing an olefin of up to about 6 carbon atoms (for example isobutylene) or a low molecular weight polyolefin derived therefrom such as diisobutylene with sulfur, sulfur monochloride, sulfur dichloride, hydrogen sulfide or combinations thereof. Sulfurized oils include sulfurized natural and synthetic oils such as mineral oils and lard oil. The sulfurized fatty acid esters are formed from a variety of fats and oils such as tall oil, linseed oil, olive oil, castor oil, peanut oil, rapeseed oil, fish oil, and the like.

The alkali metal-containing substance or alkaline earth metal-containing substance used in the process of this invention is any such compound or mixture of such compounds that is capable of dissolving elemental sulfur. Such compounds, many of which are referred to in U.S. Pat. No. 4,827,040, include alkali metal oxides, alkali metal hydroxides, alkali metal hydrosulfides, alkali metal mercaptides, and the corresponding alkaline earth metal compounds. Mixtures of two or more such alkali metal-containing compounds or of two or more such alkaline earth metal-containing compounds or of one or more such alkali metal-containing compound(s) with one or more such alkaline earth metal-containing compound(s) can be used. A few examples of such compounds are $LiOH$, $NaOH$, $KOH$, $Na_2O$, $K_2O$, $CsOH$, $MgO$, $CaO$, $Mg(OH)_2$, $Sr(OH)_2$, $BaO$, $Ba(OH)_2$, $NaSH$, $NaSCH_3$, $NaSC_2H_5$, $NaSC_6H_5$, $KSH$, $Na_2SO_3$, $K_2SO_3$, $Na_2S$, $K_2S$, and the like. As is well known, the foregoing oxides are converted into hydroxides in the presence of water and thus when using such oxides the reaction medium in which the treatment occurs will contain hydroxide ions formed by the interaction of the oxide with water. Use of sodium oxide, potassium oxide, sodium hydroxide or potassium hydroxide, or any combination of two or more of these constitutes a preferred embodiment of this invention. Another preferred embodiment involves the use of sodium sulfide or potassium sulfide or a mixture of the two as the treating agent.

The amount of treating agent used in the process can be widely varied. All that is required is to use a sufficient amount of the treating agent to cause the resultant treated organic sulfur-containing material to have reduced copper corrosiveness as compared to the same initial material not subjected to the treatment process of this invention. The optimum quantities can thus be readily determined in any given situation by the simple expedient of performing a few tests. In most cases, the treatment process will involve use of at least about 15 parts by weight of the treating agent per 100 parts by weight of the initial organic sulfur compound being treated. Amounts of treating agent in the range of about 25 to about 300 parts by weight per 100 parts by weight of organic sulfur compound being treated are typical. However, departures from these ranges are permissible whenever deemed appropriate or desirable, and are thus within the ambit of this invention.

It is possible to use any of a wide variety of ketones in forming the mixed solvent systems used in the practice of this invention. Thus use may be made of saturated acyclic aliphatic ketones, unsaturated acyclic aliphatic ketones, cycloaliphatic ketones, cyclic ketones, diketones, and the like. For best results the ketone or mixture of ketones used in the solvent system should be at least partially soluble in water or water should be at least partially soluble in the ketone(s) at the principal temperature(s) to be used in the treatment process. Ketones that are either miscible or at least highly soluble in water, such as acetone, methyl ethyl ketone, and diacetone alcohol, and the like, are preferred. However other ketones such as acetophenone, 2-heptanone, 2-hexanone, 3-hexanone, methyl isopropyl ketone, methyl isobutyl ketone, methyl isoamyl ketone, 2-pentanone, 3-pentanone, propiophenone, diisobutyl ketone, cyclohexanone, mesityl oxide, isophorone, isobutyl heptyl ketone and 2,4-pentanedione can be used. Ketones having relatively low solubility in water or relatively low solvency for water are best used in combination with another ketone or mixture of ketones that has or have high water solubility to achieve mutual solubilization. Alternatively, the ketone(s) having relatively low water solubility may be used in conjunction with other solvents having high water solubility, such as lower alcohols, tetrahydrofuran, etc., to thereby provide a substantially homogeneous liquid medium at the treatment temperature employed.

Generally speaking, the ketones used are desirably those which have a solubility in water of at least about 1% (and more preferably at least about 3%) by weight measured at 20° C. Most suitable are the water-soluble ketones containing up to about 6 carbon atoms in the molecule.

As noted above, the process of this invention is conducted in a liquid reaction medium composed at least predominantly of one or more ketones and water. The relative proportions as between the ketone(s) and the water may be varied widely provided the mixture provides sufficient solubility for the treating agent and the organic sulfur-containing material to enable the treatment process to proceed efficiently and effectively. Thus generally speaking the liquid reaction medium will contain from about 5 to about 95 volume percent of water with the balance being one or more ketones (together with mutual solubilizing cosolvent such as ethanol, isopropanol, or tetrahydrofuran, if used).

Treatment temperatures generally fall in the range of about 35° to about 150° C., and preferably in the range of about 50° to about 90° C.

The practice and advantages of this invention are further illustrated by the following examples, which are not to be construed as limiting the scope of this invention.

EXAMPLE 1

Synthesis of Di-tert-Butyl Polysulfide

Oleylamine (1.3 g) was added to 416 g (13 mols) of sulfur. To this was added dropwise with stirring over 4.25 hours a total of 900 g (10 moles, 1125 mL) of tert-butyl mercaptan at 20°–30° C. It was noticed that when 325 mL of the mercaptan had been added, the rate of hydrogen sulfide evolution had slowed. An additional 1.3 g of oleylamine was added at this point. After addition of the mercaptan was complete, the temperature was raised to 40° C. for 0.5 hr. The temperature was raised to 70° C. and kept at this temperature for 1.5 hours. Some refluxing was noticed. High vacuum was applied and the temperature was raised to 100° C. for 40 minutes. Filtration removed a fine black precipitate. The clear, yellow mobile liquid product weighed 982.7 g (85.7% yield).

EXAMPLE 2

Treatment of Dialkyl Polysulfide with Sodium Hydroxide in Water-Ketone Medium

To 66.67 g of sodium hydroxide dissolved in 300 mL of water was added 100 g of di-tert-butyl polysulfide prepared as in Example 1 dissolved in 300 mL of acetone. Heat was applied and the mixture was heated to reflux for about 1 hour. The product was then allowed to stand whereby two phases developed. The bottom aqueous phase was discarded and the organic phase was washed twice with 100 mL quantities of water. The organic phase was then subjected to rotary evaporation thereby yielding 84.26 g of di-tert-butyl polysulfide product.

Samples of the di-tert-butyl polysulfides from Examples 1 and 2 were subjected to the above copper corrosion test (3.3 hours at 121° C.). Table I summarizes the results of these tests.

TABLE I

| Di-tert-butyl polysulfide used | Copper Corrosion Tests | |
|---|---|---|
| | Copper Weight Loss, mg | Corrosion Reduction % |
| Example 1 (untreated) | 467.5 | — |
| Example 2 (treated per this invention) | 9.6 | 97.9 |

EXAMPLE 3 (COMPARATIVE)

Treatment of Dialkyl Polysulfide With Sodium Hydroxide in Water

To a solution composed of 66.67 g of sodium hydroxide dissolved in 600 mL of water was added 100 g of di-tert-butyl polysulfide prepared as in Example 1. The mixture was heated to 80° C. and held at this temperature for approximately 1 hour. The organic phase was recovered by means of a separatory funnel and washed with 100 mL of water. The resulting organic phase (the bottom layer) was separated and subjected to rotary evaporation to remove small amounts of residual water. A total of 98.21 g of a hazy di-tert-butyl polysulfide product was obtained. This was filtered to remove residual water, thereby yielding 93.88 g of product.

Another pair of copper corrosion tests using the above procedure (3 hours at 121° C.) gave the results summarized in Table II.

TABLE II

| Di-tert-butyl polysulfide used | Copper Corrosion Tests | |
|---|---|---|
| | Copper Weight Loss, mg | Corrosion Reduction % |
| Example 1 (untreated) | 502.6 | — |
| Example 3 (treated per prior art) | 491.2 | 2.3 |

EXAMPLE 4

Treatment of Sulfurized Isobutylene With Sodium Hydroxide in Water-Ketone Medium To a solution of 66.7 g of sodium hydroxide in 300 mL of water were added 100 g of sulfurized isobutylene and 300 mL of acetone. The resulting mixture was heated to reflux and refluxed for one hour. The organic and aqueous layers were separated and the organic layer was filtered and thereafter the solvent was removed by rotary evaporation yielding 91.44 g of a reddish colored product.

A sample of this treated product was subjected to the above copper corrosion test (3 hours at 121° C.). In addition, a sample of the untreated sulfurized isobutylene was tested in this manner. The untreated sulfurized isobutylene gave a copper weight loss of 69.3 milligrams. The weight loss for the treated sulfurized isobutylene was 55.8 milligrams, a reduction of almost 20% as compared to the untreated material.

The procedure of Example 4 can be applied equally well to sulfurized diisobutylene. And the procedures of Examples 2 and 4 can be performed using KOH or $Na_2S$ or $K_2S$ instead of NaOH.

The treated products of this invention are useful as extreme pressure additives for lubricating oils. They also exhibit antioxidant and antiwear properties in lubricants.

This invention is susceptible to considerable variation in its practice within the spirit and scope of the appended claims, the forms hereinbefore described constituting preferred embodiments thereof.

What is claimed is:

1. A process of reducing the copper corrosiveness of an organic sulfur-containing substance that is corrosive toward copper which comprises treating such sulfur-containing substance with an alkali metal-containing or alkaline earth metal-containing substance capable of dissolving elemental sulfur, such treatment being effected in a liquid reaction medium composed of water and at least one ketone which has a solubility in water of at least about 1% by weight measured at 20° C., whereby the treated organic sulfur-containing substance is less corrosive toward copper.

2. A process as claimed in claim 1 wherein the organic sulfur-containing substance subjected to such treatment is dihydrocarbyl polysulfide that is corrosive to copper.

3. A process as claimed in claim 2 wherein the dihydrocarbyl polysulfide subjected to such treatment is dialkyl polysulfide containing at least 3 but no more than about 18 carbon atoms in each alkyl group.

4. A process as claimed in claim 1 wherein the organic sulfur-containing substance subjected to such treatment is sulfurized olefin that is corrosive to copper.

5. A process as claimed in claim 4 wherein the sulfurized olefin subjected to such treatment is sulfurized isobutylene or sulfurized diisobutylene.

6. A process as claimed in claim 1 wherein said metal-containing substance used in such treatment consists essentially of alkali metal oxide or hydroxide, or both.

7. A process as claimed in claim 1 wherein said metal-containing substance used in such treatment consists essentially of alkali metal sulfide.

8. A process as claimed in claim 1 wherein said metal-containing substance used in such treatment consists essentially of sodium oxide, sodium hydroxide, potassium oxide, or potassium hydroxide, or a mixture of any two or more of the foregoing.

9. A process as claimed in claim 1 wherein said metal-containing substance used in such treatment is predominantly or entirely sodium hydroxide.

10. A process as claimed in claim 1 wherein the ketone used in such reaction medium is predominantly or entirely a water-soluble ketone containing up to about 6 carbon atoms in the molecule or a mixture of any two or more of such ketones.

11. A process as claimed in claim 10 wherein such ketone consists essentially of acetone, methylethylketone, or diacetone alcohol.

12. A process as claimed in claim 1 wherein the treatment is conducted at least predominantly at a temperature in the range of about 50° to about 90° C.

13. A process as claimed in claim 1 wherein the organic sulfur-containing substance subjected to such treatment consists essentially of dialkyl polysulfide which includes at least dialkyl trisulfide, dialkyl tetrasulfide and dialkyl pentasulfide and wherein said metal-containing substance used in such treatment consists essentially of alkali metal oxide or hydroxide, or both.

14. A process as claimed in claim 13 wherein said metal-containing substance used in such treatment consists essentially of sodium oxide, sodium hydroxide, potassium oxide, or potassium hydroxide, or a mixture of any two or more of the foregoing.

15. A process as claimed in claim 13 wherein said metal-containing substance used in such treatment is predominantly or entirely sodium hydroxide.

16. A process as claimed in claim 13 wherein the ketone used in such reaction medium is predominantly or entirely acetone, methylethylketone or diacetone alcohol or a mixture of any two or more of such ketones.

17. A process as claimed in claim 16 wherein such ketone consists essentially of acetone.

18. A process as claimed in claim 1 wherein said metal-containing substance used in such treatment consists essentially of alkali metal sulfide.

19. A process as claimed in claim 18 wherein said metal-containing substance used in such treatment consists essentially of sodium sulfide or potassium sulfide, or a mixture of the foregoing.

20. A process as claimed in claim 1 wherein the organic sulfur-containing substance subjected to such treatment consists essentially of sulfurized isobutylene, wherein said metal-containing substance used in such treatment consists essentially of sodium oxide, sodium hydroxide, potassium oxide, potassium hydroxide, sodium sulfide, or potassium sulfide or a mixture of any two or more of the foregoing, and wherein the ketone used in such reaction medium is a water-soluble ketone containing up to about 6 carbon atoms in the molecule.

21. A process as claimed in claim 20 wherein the ketone used in such reaction medium is predominantly or entirely acetone, methylethyl ketone or diacetone alcohol or a mixture of any two or more of such ketones.

22. A process as claimed in claim 1 wherein said ketone has a solubility in water of at least about 3% by weight measured at 20° C.

* * * * *